United States Patent [19]

Mesa et al.

[11] Patent Number: 5,354,286
[45] Date of Patent: Oct. 11, 1994

[54] INJECTION DEVICE HAVING POLYPARAXYLYLENE COATED CONTAINER

[75] Inventors: C. Michael Mesa, Boyds, Md.; N. Lawrence Dalling, Cross Junction, Va.; Sandra A. Lowery, St. Charles, Mo.; O. Napoleon Monroe, Bethesda, Md.

[73] Assignee: Survival Technology, Inc., Rockville, Md.

[21] Appl. No.: 162,294

[22] Filed: Dec. 7, 1993

[51] Int. Cl.⁵ .............................................. A61M 5/315
[52] U.S. Cl. .................... 604/230; 604/218; 604/272; 604/232
[58] Field of Search ........ 604/230, 218, 187, 132–135, 604/157, 138, 232, 272

[56] References Cited

U.S. PATENT DOCUMENTS

| | | |
|---|---|---|
| 2,832,339 | 4/1958 | Sarnoff . |
| 3,288,728 | 11/1966 | Gorham . |
| 3,300,332 | 1/1967 | Gorham et al. . |
| 3,342,754 | 9/1967 | Gorham . |
| 3,379,803 | 4/1968 | Tittmann et al. . |
| 3,882,863 | 5/1975 | Sarnoff . |
| 4,031,893 | 6/1977 | Kaplan et al. . |
| 4,225,647 | 9/1980 | Parent . |
| 4,484,910 | 11/1984 | Sarnoff et al. ..................... 604/136 |
| 4,689,042 | 8/1987 | Sarnoff et al. . |
| 4,755,169 | 7/1988 | Sarnoff et al. . |
| 4,795,433 | 1/1989 | Sarnoff . |
| 4,808,453 | 2/1989 | Romberg et al. . |
| 4,882,210 | 11/1989 | Romberg et al. . |
| 4,968,302 | 11/1990 | Schluter et al. ..................... 604/135 |
| 4,973,504 | 11/1990 | Romberg et al. . |
| 4,997,423 | 3/1991 | Okuda et al. ..................... 604/230 |
| 5,000,994 | 3/1991 | Romberg et al. . |
| 5,009,646 | 4/1991 | Sudo et al. ..................... 604/230 |
| 5,064,083 | 11/1991 | Alexander et al. . |
| 5,085,642 | 2/1992 | Sarnoff . |
| 5,092,843 | 3/1992 | Monroe . |
| 5,102,393 | 4/1992 | Sarnoff . |

Primary Examiner—John D. Yasko
Attorney, Agent, or Firm—Cushman, Darby & Cushman

[57] ABSTRACT

An injection device comprises a plastic or metal container adapted to contain a charge of medicament, the container has at least an inner surface thereof coated with polyparaxylylene. A needle is cooperable with the container so as to be communicable with the medicament and provides a passage through which the medicament can be forced into the flesh of an individual. A plunger is disposed in the container in slidably sealed relation with the polyparaxylylene coating provided on the inner surface of the container. The plunger is movable through the container toward a generally forward end thereof to force the medicament through the needle and into the flesh of the individual.

16 Claims, 2 Drawing Sheets

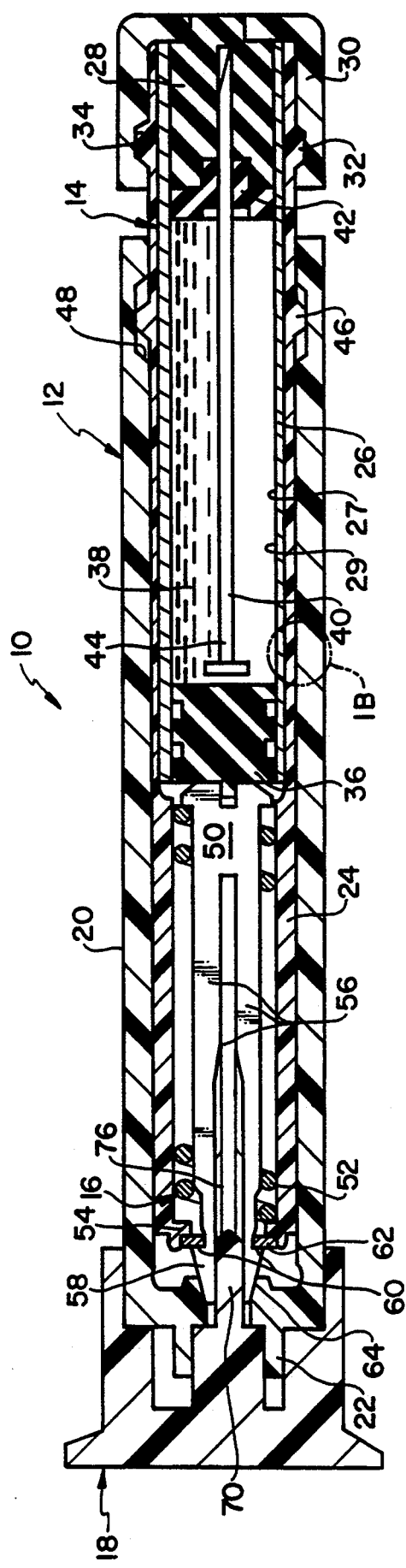
FIG. IA
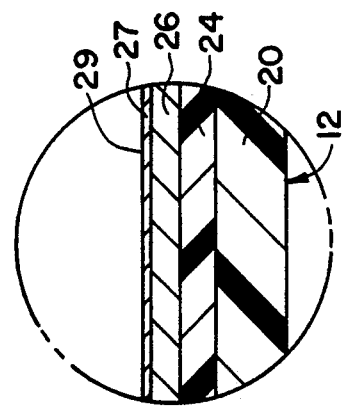
FIG. IB

INJECTION DEVICE HAVING POLYPARAXYLYLENE COATED CONTAINER

BACKGROUND OF THE INVENTION

This invention relates to the treatment of patients by medicament injection and more particularly to an improvement in injection devices such as automatic injectors and syringes.

Automatic injectors are well known. Basically, an automatic injector is a device for enabling an individual to self-administer, or administer to another, a dosage of a liquid medicament. An advantage of automatic injectors is that they contain a measured dosage of a liquid medicament in a sealed sterile condition capable of storage in such condition for an extensive period of non-use, during which period immediate injection of the stored dosage may be accomplished at any time under severe emergency conditions. Another advantage of automatic injectors is that the administration of the self-contained dosage of liquid medicament is accomplished without the necessity of the user initially seeing the hypodermic needle through which the liquid medicament is injected or of manually penetrating such a visible needle into the user's or another person's tissue. Instead, an automatic injector includes a releasable energy source, typically a stressed spring assembly. A spring assembly typically includes a stressed spring, a mechanism for releasably retaining the spring in a stressed storage position, and a releasing mechanism for releasing the releasable mechanism in response to a predetermined actuating procedure.

As stated above, automatic injectors are particularly suited for use under emergency conditions. For example, many tens of millions of such automatic injectors have been manufactured and sold containing nerve gas antidotes for use under emergency chemical warfare conditions. Typical units which have been utilized for this purpose are disclosed in U.S. Pat. Nos. 2,832,339, 3,882,863, and 4,031,893. In addition, units of this type have been manufactured and used in administering anti-arrhythmic medicaments under emergency conditions relating to heart attack medical situations. The use of an auto injector has also been proposed to provide other medicaments useful in treating heart attack symptoms such as clot selective thrombolytic agents (for example, tPA) and related medicaments. See, for example, U.S. Pat. Nos. 4,689,042, 4,755,169, and 4,795,433. Finally, automatic injectors have been marketed containing a dosage of epinephrine as an antidote for counteracting severe allergic reactions, as for example, to bee stings, and the like.

In all of these instances, the auto-injector is specifically structured so that in its normal operation, the needle extends into the muscle tissue of the user and a specified amount of liquid medicament stored in a cartridge within the injector is injected into the tissue of the user.

Since these injectors are to be used most often in emergency situations, it can be appreciated that such injectors must be very reliable in its administration of a medicament. These injectors must operate correctly even after being stored for an extensive period of time. At the same time, these injectors should be small enough and light enough to enable the user, who may be subject to an emergency condition, to easily carry the injector on his or her person at all times. It can also be appreciated that the injectors must be durable and be able to withstand shock from impact which can occur when the injector is continuously kept on a user's person, such as in the user's pocket or the like. This is especially the case when such injectors are carried by soldiers during times of warfare.

Heretofore, the cartridge for containing the medicament in most automatic injectors has been made from glass. This is primarily due to the fact that glass is highly stable and largely non-reactive with contained medicaments even after long periods of contact.

However, several problems exist with automatic injectors having glass cartridges. One major problem is that such cartridges must be specially made or uniquely protected in order to reduce the likelihood of breakage. For example, the cartridge might be made thicker and thus heavier. As a result, the automatic injector as a whole becomes somewhat larger, more costly, more complicated or all of the above. In addition, the injector becomes an inconvenience to an individual who must carry the injector at all times. Furthermore, even with making these provisions, the cartridge nevertheless remains subject to breakage. Such breakage can occur for numerous reasons. For example, the automatic injector may be dropped or otherwise exposed to severe mechanical shock. Another instance in which such breakage may occur is during filling of the cartridge with medicament. Oftentimes, the filling machines are limited in the speed at which such cartridges can be filled and then closed (with an elastic plunger or the like) due to the somewhat delicate nature of the glass material. Even with slower filling and assembly speeds, such glass cartridges are nevertheless subject to breakage. A further situation in which the glass cartridge may break is where the spring assembly provided for forcing an expelling plunger through the cartridge does so in an erratic fashion. Specifically, any bending of the spring may cause the spring to impact against the inner glass surface of the cartridge and cause breakage thereof. In addition, the mere compression of medicament within the glass cartridge during compressive expulsion of such medicament with the plunger may be sufficient to cause breakage of the cartridge if proper precautions are not taken. While the above-mentioned scenarios are extremely infrequent and unlikely, it can be appreciated that the emergency use of these injectors requires that such scenarios be limited to the fullest extent feasible.

Aside from breakage, two other problems exist with glass cartridges. First, they are relatively expensive to manufacture, and second, they are very difficult to manufacture with close tolerances.

Thus, there is a need for an automatic injector which has a cartridge made from a substance which is more durable, workable and/or less expensive than glass. In at least one instance metal has been used. Specifically, an automatic injector having a stainless steel cartridge is manufactured by the assignee of the present invention and sold under the registered trademark ATROPEN ®. While it has also been determined that plastic might be another viable alternative, it has heretofore not been widely practical as will be discussed later.

Metal and plastic both have several advantages over glass in that it can be made both thinner and lighter while at the same time stronger than glass. Thus, the automatic injector can become more durable and more reliable. However, several problems exist with providing such metal and plastic cartridges. First, metal cartridges may react with certain (if not all) medicaments (for example, lidocaine) and thereby contaminate such medicaments. With respect to plastic, a problem exists in that plastic is not completely impervious to moisture and oxygen, and therefore not well suited to store a medicament for extended periods. Thus, while it may also be desirable to use plastic in the main body of a prefilled conventional syringe (in addition to use in automatic injectors), such use has heretofore also been rather impractical for many types of medicines.

Another problem with metal, plastic, and even glass syringe and autoinjector medicament containers, is that a plunger provided therein for expelling medicament therefrom has a tendency to adhere to the side walls thereof during extended periods of non-use. For example, it has been known that a resilient plunger sitting in contact with a metallic cartridge for a significant period of time may eventually become slightly adhered to the metallic surface of the cartridge. At the same time, it has been found that the stressed spring contained within an auto-injector weakens in strength after remaining in compression for extended periods. As a result, when the auto-injector is eventually actuated, there is a possibility that the speed with which the plunger travels through the cartridge will be reduced as a result of the friction and adhesion between the plunger and cartridge. Thus, the medicament may not be dispensed at all or will be dispensed more slowly than what might otherwise be possible. This is significant since the time interval which lapses before a full dosage of medicament is dispensed may be important to the remedial results which are obtained by administration of the medicament.

It is therefore an object of the present invention to solve the problems mentioned above. These problems can be remedied by providing an automatic injector having a metallic or plastic cartridge coated by an appropriate substance. While it has been known to treat glass and other type cartridges with silicone oil or emulsion, to reduce the coefficient of friction of the sliding plunger, such silicone is undesirable. Silicone, ideally, should not be injected into a patient. In addition, such silicone does not adequately prevent metal from reacting with the medicament contained in the cartridge and does not prevent penetration of moisture and oxygen through plastic. Moreover, while silicone can be effectively baked onto the surface of glass vials or cartridges at high temperature, it has been found that silicone is more difficult to adhere to metal or plastic to provide the same lubricating effect. Therefore, to solve these problems, the present invention contemplates providing a plastic or metallic cartridge having a polyparaxylylene coating applied to at least an inner surface thereof. When such coating is applied to metal, medicament contamination is prevented, the injector is less subject to breakage than if glass were used as a container, is more reliable and efficient in plunger operation, and is less expensive to manufacture with tighter tolerances.

When such coating is applied to plastic, all the above advantages are obtained with the additional benefits associated with the barrier effect of the coating which makes the surface of plastic resistant to moisture and oxygen transmission. From this standpoint, it is a further object of the present invention to provide a syringe having a plastic body with a polyparaxylylene coating applied to at least an inner surface thereof.

Polyparaxylylene has been found to be useful in coating various materials. For example, in Romberg et al, U.S. Pat. No. 5,000,994 it is disclosed that it is useful to coat rubber closures in order to reduce ion extraction from the rubber material into the medicament and to reduce the coefficient of friction of the surface of such rubber closures to facilitate the manufacture thereof as such rubber components may become hung up on one another or on transfer equipment. This disclosure is not concerned with using polyparaxylylene to coat a non-glass container to provide a more economic, reliable, and durable container. It should also be noted that it has been found that application of polyparaxylylene to the plunger in an automatic injector may harden the elastic surface of the plunger and may have a detrimental effect on the seal between the plunger and cartridge.

Romberg et al, U.S. Pat. No. 4,882,210, on the other hand, discloses the use of polyparaxylylene for coating a glass container in order to prevent ion extraction from the glass and increase the crush strength of the glass. The disclosure addresses the fact that during assembly with a rubber stopper, glass vials are subject to breakage. The patent suggests that providing a polyparaxylylene coating to at least one side of a glass container can increase the strength of such glass container. However, this patent fails to appreciate that polyparaxylylene can effectively be used to coat other substances, such as metal and plastic, to not only obtain compatibility of such materials with medicaments, but also allows use of other materials to effectively increase the strength of a container by several orders of magnitude over that of glass.

None of the above-mentioned references contemplates coating a metallic or plastic container for medicaments, as glass has long been the material of choice for containing medicaments. Moreover, no one has ever suggested the use of such coated container for the specialized application in automatic injectors. In addition, none of the art has attempted to utilize polyparaxylylene to coat a metallic or plastic injector cartridge so that it can more easily cooperate with a plunger to more speedily and reliably dispense a medicament from a medicament cartridge, nor has the art attempted to coat the inner surface of a plastic medicament container to reduce the permeability of such housing to oxygen and moisture. This may be due to the fact that the art related to polyparaxylylene has heretofore not concerned itself with the need to carry medicaments into harsh environments such as those environments into which an automatic injector must be taken.

Therefore, it is an object of the present invention to provide an automatic injector comprising a housing having a metallic cartridge contained therein. The cartridge has at least an inner surface thereof provided with a polyparaxylylene coating. A charge of medicament is contained within the metallic cartridge and in communication with the polyparaxylylene coating, which reduces the coefficient of friction of the inner surface of the cartridge and prevents metallic ions from being extracted from the cartridge and into the medicament. A plunger is normally disposed in a generally rearward end of the metallic cartridge, and is movable through the cartridge toward a generally forward end thereof in response to a predetermined actuating procedure. The movable plunger rearwardly confines the medicament within the metallic cartridge and is in slidable sealed relation with the polyparaxylylene coating provided on the metallic cartridge. The polyparaxylylene coating reduces the tendency of the plunger to adhere to the inner surface and reduces the time required for the plunger to travel from the generally rearward end to the generally forward end of the metallic cartridge. A needle is normally disposed within the housing and is projectable from a forward end of the housing and communicable with the medicament so that movement of the plunger through the cartridge forces the medicament through the needle and into the tissue of a user in response to the predetermined actuating procedure. In addition, a releasable energy source is releasable in response to the predetermined actuating procedure to project the needle and slidingly drive the plunger through the metallic sealed relation to expel the medicament through the needle and into the tissue of the user.

It is a further object of the present invention to provide a plastic housing for an automatic injector and/or syringe to limit permeability thereof to oxygen and moisture.

In another aspect of the present invention, it can be appreciated that certain of the aforementioned automatic injectors are provided with a metallic needle that is normally stored in contact with a medicament. Such type of injectors are disclosed in our previously granted U.S. Pat. Nos. 4,484,910, 5,085,642, and 5,092,843. An advantage of such injectors is that they have a shorter axial length than other type of injectors that have the needle normally stored in a separately provided chamber disposed forwardly of the medicament (e.g. see our previously granted U.S. Pat. No. 5,102,393). As stated previously, metal cartridges may react with certain medicaments, such as lidocaine, and thereby contaminate such medicaments. To solve the problem associated with such contamination, it is a further object of the present invention to provide an automatic injector which comprises a housing, a cartridge contained within the housing, a charge of medicament contained in the cartridge, and a needle normally disposed within the cartridge so as to be in communication with the medicament. The needle is provided with a polyparaxylylene coating for preventing ions from being extracted from the needle into the medicament. The needle is projectable from a forward end of the housing, while a plunger is normally disposed in a generally rearward end of the cartridge and movable through the cartridge in response to a predetermined actuating procedure so as to force the medicament through the needle and into the flesh of an individual. In addition, a releasable energy source is releasable in response to the predetermined actuating procedure to project the needle from the forward end of the housing and drive the plunger through the cartridge to expel the medicament through the needle and into the flesh of the individual.

These and other objects of the present invention will become more apparent during the course of the following detailed description and appended claims. The invention may be best understood with reference to the accompanying drawings wherein illustrative embodiments are shown.

BRIEF DESCRIPTION OF THE DRAWINGS

FIG. 1 is a longitudinal sectional view, with a portion thereof shown enlarged, of an automatic injector embodying the principles of the present invention.

DETAILED DESCRIPTION OF THE DRAWINGS

Figure 2:
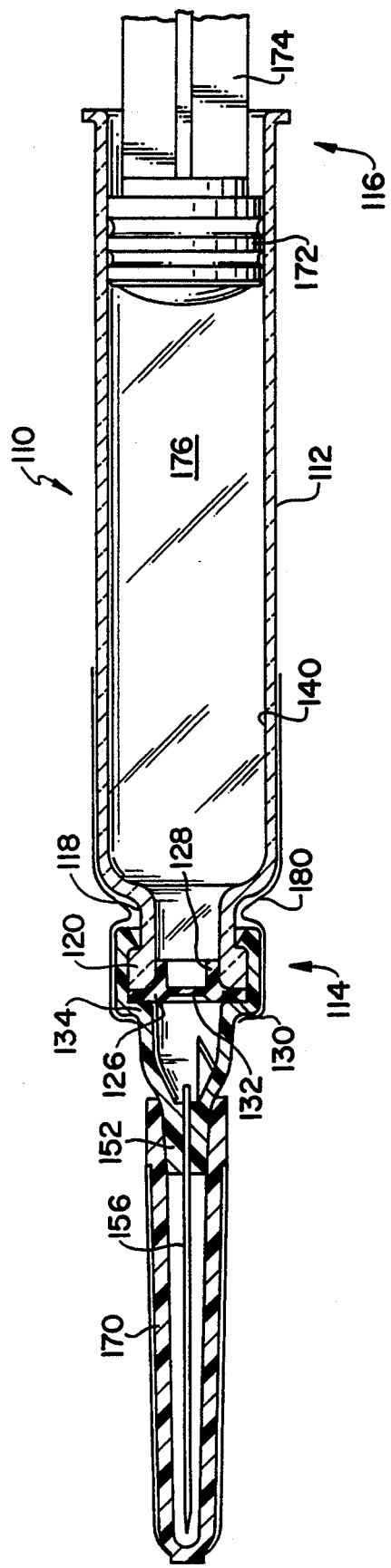
FIG. 2 is a longitudinal sectional view of a syringe which embodies the principles of the present invention.

An automatic injector, generally indicated at 10 embodies the principles of the present invention. The injector 10 includes a tubular housing 12, a medicament injecting assembly, generally indicated at 14, within the forward end portion of the housing assembly 12, and a releasable energy source which is releasable in response to a predetermined actuating procedure as will be described more fully later. While the releasable energy source can be any type of assembly which effectuates an injection operation (e.g. a compressed gas assembly as disclosed in our U.S. Pat. No. 4,518,384), it is preferred that the releasable energy source be a stressed spring assembly, as generally indicated at 16. The stressed spring assembly is disposed within the rearward end portion of the housing assembly 12 in operative relation with the medicament injecting assembly 14. A releasable end safety cap 18 positioned at the rear of the housing assembly 12 is in operative relation with the stressed spring assembly 16.

The housing assembly 12, medicament injecting assembly 14, and stress spring assembly 16 are generally constructed in accordance with the teachings of U.S. Pat. No. 2,832,339. As shown in FIG. 1, the housing assembly includes a cylindrical outer housing member 20 having a centrally apertured cylindrical rear wall portion 22 of reduced diameter on which the safety end cap 18 is mounted. The housing assembly 12 also includes an inner cylindrical housing member 24 within the housing member 20 within which is mounted the medicament injecting assembly 14 and the stressed spring assembly 16. The forward portion of the inner housing member 24 is formed with a counterbore for receiving therein a cylindrical dosage container or cartridge 26. This cartridge is made either of a metallic or plastic material. The preferred metallic materials are stainless steel and aluminum, while the preferred plastic material is polypropylene. Cartridge 26 has an inner surface 27 which is coated with a continuous poly (p-xylylene) or polyparaxylylene coating 29 (see, exploded portion of FIG. 1).

This coating is preferably provided to the cartridge or container by a process in which the polymer is deposited onto the cartridge from the vapor phase in a manner which resembles vacuum metallization. Unlike vacuum metallization, however, which is conducted at pressures of $10^{-5}$ tort or below, the polyparaxylylene coating is formed at around 0.1 torr. Such coating is also known as Parylene and is provided by Specialty Coating Systems, Inc. of Indianapolis, Ind. As a result of the procedure in which the polyparaxylylene is applied to the cartridge 26, it can be appreciated that the outer surface of the cartridge may also be coated. However, steps could be taken to prevent the coating of the outer surface if so desired.

It has been found that Polyparaxylylene has several useful properties, such as low permeability to oxygen and moisture, low coefficient of friction, high durability at high temperatures (expected lifetime of approximately ten years at 100 degrees Celsius), high resistance to impact at cryogenic temperatures, high chemical resistance, and excellent adhesion to the surface it is provided to.

In the broadest sense, the polyparaxylylene should have a thickness of between about 0.00001 to 0.001 inches. In the case of metal, the coating preferably ranges from 0.00005 to 0.0003 inches, and in the case of plastic, it is preferred that the coating range from 0.00007 to 0.0005 inches in thickness. The polyparaxylylene coatings in the present invention have preferred thicknesses ranging between a minimal level of acceptable intended functionality and a maximum level beyond which any added functionality which might be obtained from additional thickness is not worth the added cost of material required to obtain such increased thickness.

The forward end of the container or cartridge 26 is closed by a stopper or plug 28 of suitable rubber or plastic material. Plug 28 is retained in closing relation with the forward end of the cartridge 26 by a housing end cap member 30 of molded plastic material. The cap is retained on the inner housing member 24 by inter-engagement of a pair of ridges 32 formed on the exterior periphery of the tubular member 24 with an annular groove 34 formed on the interior periphery of the cap member 30. The rearward end of the cartridge 26 is closed by a plunger 36 which is slidably, sealingly engaged with the polyparaxylylene coating 29 at the rearward end of the cartridge so as to enclose within the cartridge a dosage 38 of a liquid medicament. The polyparaxylylene coating 29 reduces the coefficient of friction of the inner surface 27 of the cartridge 26 and eases movement of the plunger when the plunger is forced forwardly through cartridge 26 (towards the right in FIG. 1). Preferably, plunger 36 is coated with a substance which prevents extraction of metallic ions therefrom into the medicament 38 and further helps the plunger move through cartridge 26 during an injection. Such coating must be made of a material which is medicament compatible. While the coating can be polyparaxylylene, it is preferably made of some other medicament compatible substance as it has been found that polyparaxylylene may harden the outer surface of the elastic plunger to the extent that the plunger is unable to make an effective seal with the cartridge.

A hypodermic needle 40 is disposed within the cartridge 26. As can be discerned from FIG. 1, needle 40 is normally stored in contact with the medicament 38. However, in the broadest aspects of the present invention, it can be appreciated that needle 40 can be disposed in a separate chamber (either evacuated or filled with a preferably inert gas) forwardly of the medicament 38 (for example, see our U.S. Pat. No. 5,085,642 and 5,102,393), so long as the needle is somehow communicable with the medicament in a manner which permits the medicament to travel through the needle and into the flesh of an individual. The needle can also be disposed in contact with one of two medicaments, which are normally stored separately within the injector and then either mixed within the injector prior to an injection (e.g. see U.S. Pat. No. 5,041,088) or injected separately one after the other (see U.S. Pat. No. 5,092,843). The hypodermic needle 40 is preferably made from stainless steel. In the instance in which the needle is stored in contact with the medicament, as described above, it is preferred that the needle be coated with a layer of polyparaxylylene to prevent ions from being extracted from the needle and into the medicament. Both the external surface of the needle (visible in FIG. 1) and the internal surface (defining the inner path through the needle) can be coated.

The needle 40 has its pointed end disposed within a recess formed in the plug 28. A disc 42 of plastic is disposed within the forward end of the cartridge 26 in surrounding sealed relation with the hypodermic needle 40 and in abutting engagement with the plug 28. The disc serves to releasably hold the needle in its storage position to provide peripheral centering therefor during the dosage injecting stroke of the plunger 36. The rearward end of the hypodermic needle 40 is enlarged for engagement by the plunger and has a slot 44 formed in its periphery adjacent the enlarged end for communicating the dosage 38 with the hollow interior of the hypodermic needle 40 when the plunger 36 is in engagement therewith. The inner housing member 24 is mounted within the outer housing member 20 for limited reciprocating movement as determined by a pair of ridges 46 formed on the exterior periphery of the tubular inner housing member 24 at a position spaced rearwardly from the pair of ridges 32. The pair of ridges 46 is adapted to engage with an elongated annular groove 48 formed on the interior periphery of the outer housing member 20.

The stressed spring assembly 16 includes a normally compressed but releasable coil spring 52 and an elongated collet member 50 made up of two interfitted stampings. The collet member is disposed within the rearward portion of the housing member 24 and has its forward end disposed in abutment with the plunger 36. The forward end of the collet member 50 is also exteriorly configured to engage the forward end of the stressed coil spring 52 which surrounds the central portion of the elongated collet member 50 within the inner housing member 24 and has its rearward end engaged with an apertured end wall formed integrally on the rearward end of the inner housing member 24.

The rearward ends of the stampings of the elongated collet member 50 are split to provide four laterally movable spring fingers 56, the rearward extremities of which are formed with rearwardly and outwardly facing cam releasing surfaces 58. Extending inwardly from the forward end of each cam surface 58 is a locking shoulder 60 adapted to engage a locking ring 62 seated on the rear surface of the centrally apertured rear wall 54. The forward portion of the apertured cylindrical wall portion 22 is formed with a frusto-conical surface 64 which is disposed in engagement with the cam surfaces 58 so as to effect a laterally inward movement of the spring fingers toward one another to disengage locking shoulders 60 from locking ring 62 in response to a relative forward actuating movement of the outer housing member 20 with respect to the inner housing member 24.

The operation of the injector will now be described. In the first step of operation, releasable end cap 18 is removed from the injector 10. This removal is accomplished simply by gripping the exterior periphery of the end cap 18 and moving it rearwardly while gripping and holding the outer housing member 20. The removal of the cap member 18 carries with it a safety pin portion 70. With the safety pin portion 70 removed from its safety position which normally prevents the laterally inward movement of the spring fingers 56, the user can now complete the operation by moving the forward cap member 30 into contact with the tissue of a person to be injected. By applying a continued forward force on the exterior periphery of the outer housing member 20, cam surfaces 64 thereof are moved forwardly with respect to the locking ring 62. This forward movement in cooperation with the cam surfaces 58 on the spring fingers 56 causes the locking surfaces 60 of the latter to move laterally inwardly of the locking ring 62 thus releasing the stressed spring 52. The spring 52 acts through the collet member 50 to move the same forwardly which has the effect of moving the plunger 36 with it. As the plunger moves forwardly, it carries with it the needle 40. The pointed forward end of the needle pierces through the plug 28 and into the muscle tissue of the patient. At the same time, the dosage 38 of liquid medicament within the cartridge 26 is caused to move inwardly into the slot 44 of the needle and outwardly of the pointed forward end thereof as the same moves into the muscle tissue of the user. After the forward movement of the plunger has been completed, the user simply withdraws the needle 40 rearwardly.

As a result of the provision of the polyparaxylylene coating to the injector cartridge, the durability, operation, reliability, and medicament compatibility are greatly improved as previously described.

In FIG. 2, there is shown a hypodermic syringe 110 which embodies the principles of the present invention. This syringe is similar to that described in our previous U.S. Pat. No. 4,747,839, which is hereby incorporated by reference, with the exception that this previous patent relates only to syringes with a glass container or barrel.

The hypodermic syringe 110 of the present invention comprises a cylindrical plastic barrel 112 which is open at both the forward and rearward ends 114 and 116 respectively. The forward tooled end has a necked-down portion 118 terminating in an enlarged annular flange 120 having its outer diameter greater than that of the necked down portion 118 and less than that of the plastic cylindrical barrel 112. The diameter of the opening in the annular flange 120 is equal to that in the necked down portion 118 and less than that of cylindrical barrel 112.

A stopper 126 is positioned in the forward end of the cylindrical barrel 112 to close off the opening in that end. The stopper 126 comprises a cylindrical plug portion 128 fitting into the opening formed by the inside diameter of the annular flange 120 and the necked down portion of the cylindrical barrel 112. The cylindrical plug portion 128 of the stopper 126 is closed off by a flat disc like cap 130 having a diameter generally equal to the outer diameter of the annular flange 120 and resting thereon. The forward end 114 of the cylindrical barrel 112 is thus closed by stopper 126. The center portion 132 of the stopper 126 is provided with an area of reduced thickness to assist in the bursting of the stopper when the syringe is activated.

A plastic needle hub 134 is resiliently fitted onto the annular flange 120 of the cylindrical barrel 112. A tapered portion 152 is integrally formed with hub 134 and is sized to receive a needle 156. A suitable needle guard 170 is positioned over the needle 156 and is slidably affixed to tapered portion 152.

The rearward open end of the cylindrical barrel 112 is closed off by a slidable plunger 172 which has a rearward operating member 174. The space between the stopper 126 and the plunger forms a medicament chamber 176.

The cylindrical barrel 112 has at least its inner surface 140 coated with a layer of polyparaxylylene to inhibit permeability of the plastic material composing the barrel. While coating the outer surface of the barrel 112 would also be effective in preventing permeability to oxygen and moisture, it is preferable for the inner surface 140 to be coated to also promote compatibility with the medicament and reduce the coefficient of friction thereof. In any event, as earlier described, both the inner and outer surfaces of the container are normally coated.

With the provision of the polyparaxylylene coating, a highly durable inexpensive, and material compatible syringe can be made.

For purposes of background and elaboration of the present disclosure, the disclosures of the patents mentioned herein are incorporated by reference into the present specification.

It thus will be seen that the objects of this invention have been fully and effectively accomplished. It will be realized, however, that the foregoing preferred specific embodiment has been shown and described for the purpose of illustrating the functional and structural principles of this invention, and is subject to change without departure from such principles. Therefore, this invention includes all modifications encompassed within the spirit and scope of the following claims.

What is claimed is:

1. An automatic injector comprising:
   a housing;
   a metallic cartridge contained within said housing, said cartridge having at least an inner surface thereof coated with polyparaxylylene to reduce the coefficient of friction of said inner surface;
   a charge of medicament contained in said metallic cartridge and in communication with said polyparaxylylene coating, said polyparaxylylene coating preventing ions from being extracted from said metallic cartridge into said medicament;
   a plunger normally disposed in a generally rearward end of said metallic cartridge and movable through said metallic cartridge toward a generally forward end thereof in response to a predetermined actuating procedure, said movable plunger rearwardly confining said medicament within said metallic cartridge and being in slidable sealed relation with said polyparaxylylene coating provided on said metallic cartridge, said polyparaxylylene coating sufficiently reducing the coefficient of friction of said inner surface to reduce the time required for said plunger to travel from said generally rearward end to said generally forward end of said metallic cartridge;
   a needle normally disposed within said housing, said needle being projectable from a forward end of said housing and communicable with said medicament so that movement of said plunger through said cartridge forces said medicament through said needle and into the flesh of an individual in response to said predetermined actuating procedure; and
   a releasable energy source releasable in response to said predetermined actuating procedure to project said needle from the forward end of the housing and slidingly drive said plunger through said metallic cartridge in sealed relation to expel said medicament through said needle and into the flesh of an individual.

2. The automatic injector as claimed in claim 1, wherein said metallic material is made from stainless steel.

3. The automatic injector as claimed in claim 1, wherein said metallic material is made from aluminum.

4. The automatic injector as claimed in claim 1, wherein said polyparaxylylene coating has a thickness between about 0.00001 to 0.001 inches.

5. The automatic injector as claimed in claim 4, wherein said polyparaxylylene coating has a thickness between about 0.00005 to 0.0003 inches.

6. The automatic injector as claimed in claim 1, wherein said needle is normally stored in contact with said medicament.

7. The automatic injector as claimed in claim 6, wherein said needle is provided with a coating of polyparaxylylene.

8. The automatic injector as claimed in claim 1, wherein said releasable energy source comprises a normally compressed spring which is decompressed in response to said predetermined actuating procedure.

9. An injection device comprising:
 a plastic container having at least an inner surface thereof coated with polyparaxylylene to reduce the permeability of said plastic container to oxygen and moisture, said plastic container adapted to contain a charge of medicament in communication with said polyparaxylylene coating;
 a needle cooperable with said container so as to be communicable with said medicament and providing a passage through which said medicament can be forced into the flesh of an individual; and
 a plunger disposed in said plastic container in slidably sealed relation with said polyparaxylylene coating provided on said inner surface of said container, said plunger being movable through said plastic container toward a generally forward end thereof to force said medicament through said needle and into the flesh of the individual.

10. An injection device as claimed in claim 9, further comprising:
 a housing for containing said plastic container, said needle being normally disposed within said housing and projectable from a forward end thereof in response to a predetermined actuating procedure; and
 a releasable energy source releasable in response to said predetermined actuating procedure to project said needle from the forward end of the housing and drive said plunger through said plastic container to force said medicament through said needle and into the flesh of an individual.

11. The automatic injector as claimed in claim 10, wherein said releasable energy source comprises a normally compressed spring which is decompressed in response to said predetermined actuating procedure.

12. An injection device as claimed in claim 9, wherein said plunger is substantially elongate and has a rearward end thereof projecting from said container for manual engagement so that said plunger can be manually moved through said plastic container toward the generally forward end thereof to force said medicament through said needle and into the flesh of the individual.

13. The automatic injection as claimed in claim 9, wherein said polyparaxylylene coating has a thickness between about 0.00007 to 0.0005 inches.

14. The automatic injector as claimed in claim 13, wherein said polyparaxylylene coating has a thickness between about 0.00001 to 0.001 inches.

15. An automatic injector comprising:
 a housing;
 a cartridge contained within said housing;
 a charge of medicament contained in said cartridge;
 a needle normally disposed within said cartridge so as to be in communication with said medicament, said needle being provided with a polyparaxylylene coating for preventing ions from being extracted from said needle into said medicament, said needle being projectable from a forward end of said housing;
 a plunger normally disposed in a generally rearward end of said cartridge and movable through said cartridge in response to a predetermined actuating procedure so as to force said medicament through said needle and into the flesh of an individual; and
 a releasable energy source which is releasable in response to said predetermined actuating procedure to project said needle from the forward end of the housing and drive said plunger through said cartridge to expel said medicament through said needle and into the flesh of an individual.

16. The automatic injector as claimed in claim 15, wherein said releasable energy source comprises a normally compressed spring which is decompressed in response to said predetermined actuating procedure.

* * * * *